United States Patent
Yui et al.

(10) Patent No.: US 12,405,277 B2
(45) Date of Patent: Sep. 2, 2025

(54) HEMOGLOBIN ASSAY REAGENT, ASSAY KIT AND ASSAY METHOD

(71) Applicant: EIKEN KAGAKU KABUSHIKI KAISHA, Tokyo (JP)

(72) Inventors: Megumi Yui, Tochigi (JP); Mitsuru Makinodan, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 921 days.

(21) Appl. No.: 17/278,647

(22) PCT Filed: Sep. 13, 2019

(86) PCT No.: PCT/JP2019/036235
§ 371 (c)(1),
(2) Date: Mar. 22, 2021

(87) PCT Pub. No.: WO2020/066722
PCT Pub. Date: Apr. 2, 2020

(65) Prior Publication Data
US 2022/0043008 A1  Feb. 10, 2022

(30) Foreign Application Priority Data
Sep. 26, 2018 (JP) ................. 2018-179952

(51) Int. Cl.
*G01N 33/72* (2006.01)
*G01N 33/545* (2006.01)
*G01N 33/553* (2006.01)

(52) U.S. Cl.
CPC ......... *G01N 33/721* (2013.01); *G01N 33/545* (2013.01); *G01N 33/553* (2013.01)

(58) Field of Classification Search
CPC .. G01N 33/721; G01N 33/545; G01N 33/553; G01N 2474/00; G01N 33/72; G01N 33/54306; G01N 33/563; C07K 16/18
USPC ......................................... 436/66
See application file for complete search history.

(56) References Cited

U.S. PATENT DOCUMENTS

2020/0319183 A1   10/2020   Yasui et al.

FOREIGN PATENT DOCUMENTS

| | | | |
|---|---|---|---|
| EP | 0215401 | * | 3/1987 |
| EP | 0448072 A2 | | 9/1991 |
| EP | 3467498 A1 | | 4/2019 |
| JP | H2-193071 A | | 7/1990 |
| JP | H02231565 A | | 9/1990 |
| JP | H2-296149 A | | 12/1990 |
| JP | H3-272698 A | | 12/1991 |
| JP | H5-322889 A | | 12/1993 |
| JP | H05322888 A | | 12/1993 |
| JP | H07103978 A | | 4/1995 |
| JP | H08313530 A | | 11/1996 |
| JP | H11201969 A | * | 7/1997 |
| JP | H10-132824 A | | 5/1998 |
| JP | H 11201969 | * | 7/1999 |
| JP | H11-218533 A | | 8/1999 |
| JP | H11-242027 A | | 9/1999 |
| JP | 2010014586 | * | 1/2010 |
| JP | 2010014586 A | * | 1/2010 |
| JP | 2016-191580 A | | 11/2016 |
| TW | 201932838 A | | 8/2019 |
| WO | 2010013525 A1 | | 2/2010 |
| WO | 2017/209001 A1 | | 12/2017 |

OTHER PUBLICATIONS

TruQuickTM Hb+Hb/Hp Combo 25T. A rapid, one-step test for the qualitative detection hemoglobin and haptoglobin-hemoglobin complex. Sep. 2017. (Year: 2017).*
Patent Cooperation Treaty, International Search Report issued in PCT/JP2019/036235, Dec. 10, 2019, pp. 1-2.
Patent Cooperation Treaty, International Preliminary Report on Patentability issued in PCT/JP2019/036235, Mar. 23, 2021, pp. 1-7.
Meguro, Takashi, "Measurement of Fecal Hemoglobin-Haptoglobin Complex as a New Diagnostic Tool of Lower Gastroin", The Hokkaido Journal of Medical Science, 1994, pp. 995-1009, vol. 69(4).

* cited by examiner

*Primary Examiner* — Jill A Warden
*Assistant Examiner* — Jacqueline Brazin
(74) *Attorney, Agent, or Firm* — Pillsbury Winthrop Shaw Pittman LLP

(57) ABSTRACT

An object of the present invention is to provide a hemoglobin measurement reagent and measurement method that allow for more accurate measurement of the amount of hemoglobin by suppressing a decrease in a measured value of hemoglobin triggered by the addition of haptoglobin. The reagent for measuring hemoglobin of the present invention includes: an insoluble carrier immobilizing an anti-hemoglobin antibody; and an insoluble carrier immobilizing an anti-haptoglobin antibody. The method for measuring hemoglobin in a specimen of the present invention includes: a step (1) of mixing a specimen with haptoglobin and forming a hemoglobin-haptoglobin complex to obtain a sample containing the hemoglobin-haptoglobin complex; and a step (2) of bringing the sample obtained in the step (1) into contact with the insoluble carrier immobilizing an anti-hemoglobin antibody and the insoluble carrier immobilizing an anti-haptoglobin antibody to cause immunoagglutination.

15 Claims, No Drawings

HEMOGLOBIN ASSAY REAGENT, ASSAY KIT AND ASSAY METHOD

RELATED PATENT APPLICATIONS

This patent application is a national phase filing of, and claims the benefit of, International Patent Application No. PCT/JP2019/036235, filed on Sep. 13, 2019, which claims priority to Japanese Patent Application No. 2018-179952, filed on Sep. 26, 2018, the contents of which are hereby incorporated by reference in their entirety.

TECHNICAL FIELD

The present invention relates to a hemoglobin measurement reagent and a measurement method.

BACKGROUND ART

Detection of blood contained in specimens such as feces, urine, and saliva is useful for diagnosis of many diseases. For example, a fecal occult blood test for detecting blood in feces is used for screening for colorectal cancer. An immunological method for detecting hemoglobin contained in occult blood in a specimen such as feces using an anti-hemoglobin antibody is known as a method for detecting occult blood.

A specimen to be used for an occult blood test is usually collected by a subject in a container containing a preservation solution, and sent to an inspection institution such as a hospital. In many cases, a preservation solution containing a specimen is stored for several days until it is actually used for a test, and often placed in a high temperature environment during that period. Hemoglobin is unstable in solution, and is particularly easily denatured and degraded under high temperature conditions. In a case where a structure of an epitope or a surrounding site thereof changes due to denaturation or degradation of hemoglobin, an antibody cannot recognize hemoglobin. Accordingly, the accuracy of detection of hemoglobin by an immunological method decreases.

Therefore, a method for adding haptoglobin to a specimen preservation solution is used (for example, Patent Literature 1) for stabilizing hemoglobin. Haptoglobin is a protein which is present in the blood of a wide range of animals and plays a role of recovering hemoglobin released into blood due to hemolysis of red blood cells. It is known that haptoglobin rapidly irreversibly binds to hemoglobin to form a stable hemoglobin-haptoglobin complex. In a case where haptoglobin has been previously added to a preservation solution or the like, hemoglobin contained in the specimen is stabilized by a hemoglobin-haptoglobin complex being formed when the specimen is added to a preservation solution or the like.

However, in the case of adding haptoglobin, especially when an excess amount of haptoglobin with respect to free hemoglobin in the specimen is added thereto, a decrease in a measured value of hemoglobin is sometimes recognized (Patent Literature 1).

CITATION LIST

Patent Literature

[Patent Literature 1] Japanese Unexamined Patent Publication No. H10-132824

SUMMARY OF INVENTION

Technical Problem

An object of the present invention is to provide a hemoglobin measurement reagent and measurement method capable of suppressing a decrease in a measured value of hemoglobin due to addition of haptoglobin to more accurately measure the amount of hemoglobin.

Solution to Problem

The present inventors have conducted extensive studies in order to solve the above-described problems of the related art. As a result, they have found that a decrease in a measured value of hemoglobin due to addition of haptoglobin can be suppressed by making an insoluble carrier to which an anti-hemoglobin antibody binds and an insoluble carrier to which an anti-haptoglobin antibody binds coexist and that the amount of hemoglobin can be more accurately measured, and have completed the present invention.

That is, the present invention relates to, for example, each of the following inventions.

[1] A reagent for measuring hemoglobin, including: an insoluble carrier immobilizing an anti-hemoglobin antibody; and an insoluble carrier immobilizing an anti-haptoglobin antibody.

[2] The reagent according to [1], in which the number of kinds of the anti-hemoglobin antibodies is at least two.

[3] The reagent according to [1] or [2], in which the insoluble carriers are latex particles and/or colloidal gold particles.

[4] The reagent according to any one of [1] to [3], in which the anti-hemoglobin antibody and the anti-haptoglobin antibody are monoclonal antibodies.

[5] The reagent according to any one of [1] to [4], in which the number of kinds of the anti-haptoglobin antibodies is one.

[6] A hemoglobin measurement method for measuring hemoglobin in a specimen, the method including: a step (1) of mixing a specimen with haptoglobin and forming a hemoglobin-haptoglobin complex to obtain a sample containing the hemoglobin-haptoglobin complex; and a step (2) of bringing the sample obtained in the step (1) into contact with the insoluble carrier immobilizing an anti-hemoglobin antibody and the insoluble carrier immobilizing an anti-haptoglobin antibody to cause immunoagglutination.

[7] The measurement method according to [6], in which the number of kinds of the anti-hemoglobin antibodies is at least two.

[8] The measurement method according to [6] or [7], in which the insoluble carriers are latex particles and/or colloidal gold particles.

[9] The measurement method according to any one of [6] to [8], in which the anti-hemoglobin antibody and the anti-haptoglobin antibody are monoclonal antibodies.

[10] The measurement method according to any one of [6] to [9], in which the specimen is feces, saliva, or urine.

[11] The measurement method according to any one of [6] to [10], in which haptoglobin is contained in a specimen preservation solution.

[12] The measurement method according to [11], in which a concentration of haptoglobin in the specimen preservation solution is 0.05 units/L to 50 units/L.

[13] The measurement method according to any one of [6] to [12], in which hemoglobin in the specimen contains at least one selected from the group consisting of free hemoglobin, a hemoglobin-haptoglobin complex intermediate, and a complete hemoglobin-haptoglobin complex, and at least a part of the free hemoglobin forms the hemoglobin-haptoglobin complex intermediate and/or the complete hemoglobin-haptoglobin complex together with the haptoglobin after the step (1).

[14] A method for measuring hemoglobin in a specimen, the method including: a step of bringing a specimen into contact with an insoluble carrier immobilizing an anti-hemoglobin antibody and an insoluble carrier immobilizing an anti-haptoglobin antibody to cause immunoagglutination.

[15] A method for suppressing a decrease in a measured value of hemoglobin in a specimen, the method including: a step of bringing a specimen into contact with an insoluble carrier immobilizing an anti-hemoglobin antibody and an insoluble carrier immobilizing an anti-haptoglobin antibody to cause immunoagglutination.

[16] A kit for measuring hemoglobin in a specimen, the kit including: an insoluble carrier immobilizing an anti-hemoglobin antibody; an insoluble carrier immobilizing an anti-haptoglobin antibody; and haptoglobin.

[17] A kit for measuring hemoglobin in a specimen, the kit including: the reagent according to any one of [1] to [5]; and haptoglobin.

Advantageous Effects of Invention

According to the present invention, a measurement reagent and a measurement method capable of more accurately measuring the amount of hemoglobin is provided.

DESCRIPTION OF EMBODIMENTS

Definition

[Hemoglobin-Haptoglobin Complex]

Hemoglobin is a protein which is present in red blood cells, and has a tetrameric structure $[\alpha_2\beta_2]$ consisting of two sets of two subunits called an $\alpha$ subunit (or an $\alpha$ chain) and a $\beta$ subunit (or a $\beta$ chain). Haptoglobin is a protein, which is present in plasma and binds to hemoglobin released in blood, and has three types of structures. For example, type 1-1 haptoglobin has a tetrameric structure $[\alpha_2\beta_2]$ consisting of two sets of two subunits called an $\alpha$ subunit (or an $\alpha$ chain) and a $\beta$ subunit (or a $\beta$ chain).

Hemoglobin and haptoglobin form a stable complex. In general, one molecule of hemoglobin binds to one molecule of haptoglobin. Such a complex is called a hemoglobin-haptoglobin complex, and is also called a complete hemoglobin-haptoglobin complex in the present specification.

On the other hand, in a case where a molar ratio (hemoglobin:haptoglobin) of hemoglobin to haptoglobin becomes less than 1, that is, in a case where haptoglobin is present in an excess amount with respect to hemoglobin, a complex called a hemoglobin-haptoglobin complex intermediate tends to be formed (J. V. PASTEWKA et al., Biochimica et Biophysica Acta, 386 (1975) 530-537). When forming the hemoglobin-haptoglobin complex intermediate, it is thought that one molecule of tetrameric hemoglobin $[\alpha_2\beta_2]$ dissociates into two molecules of dimers $(\alpha\beta)$ and each $\alpha\beta$ dimer binds to one molecule of haptoglobin. That is, it is thought that the hemoglobin-haptoglobin complex intermediate is a complex in which ½ molecule of hemoglobin $(\alpha\beta)$ binds to one molecule of haptoglobin $[\alpha_2\beta_2]$.

In the present specification, the hemoglobin-haptoglobin complex contains both a complete hemoglobin-haptoglobin complex and a hemoglobin-haptoglobin complex intermediate unless otherwise specified.

[Specimen]

The specimen in the present specification is a biological sample which is taken from a test object and contains or may contain hemoglobin. The specimen may be feces, saliva, or urine, and is particularly preferably feces. In addition, whole blood, serum, plasma, or the like can be used as a specimen, and measurement of the amount of hemoglobin thereof can be useful as an index of, for example, hemolysis or treatment using a haptoglobin preparation.

[Sample]

The sample in the present specification contains a specimen, and is particularly obtained by mixing a specimen with haptoglobin. Free hemoglobin in a specimen forms a stable hemoglobin-haptoglobin complex by being mixed with haptoglobin.

That is, free hemoglobin which has not formed a complex with haptoglobin, a hemoglobin-haptoglobin complex (hemoglobin-haptoglobin complex derived from a specimen) which was originally present in the specimen, and/or a hemoglobin-haptoglobin complex (prepared hemoglobin-haptoglobin complex) formed by addition of haptoglobin can be contained in the sample.

In particular, in the sample obtained by mixing a specimen with haptoglobin, a prepared hemoglobin-haptoglobin complex is preferably formed such that all free hemoglobin forms a complex with haptoglobin, and the sample preferably consists of a hemoglobin-haptoglobin complex derived from a specimen and a prepared hemoglobin-haptoglobin complex, from the viewpoint of stability.

The sample is obtained such that, for example, a subject or the like collects a specimen, the specimen being then immediately added to a specimen preservation solution (hereinafter, referred to as a "preservation solution" depending on the circumstances) containing haptoglobin. The sample may be stored at normal temperature for several days until measurement of hemoglobin, and is preferably stored in a refrigerator at 2° C. to 10° C. In a case where the specimen is feces or the like containing a solid matter, the solid matter may be removed by filtering the preservation solution and used as a sample.

[Preservation Solution]

The preservation solution means a specimen preservation solution for preserving a specimen and preferably contains haptoglobin.

It is preferable that the preservation solution further contains a buffer solution or the like. The preservation solution or the like may be a buffer solution containing a good buffer agent such as 2-morpholinoethanesulfonic acid (MES), 2-[4-(2-hydroxyethyl)-1-piperazinyl-ethanesulfonic acid (HEPES), or piperazine-1,4-bis(2-ethanesulfonic acid) (PIPES), or may be a phosphate buffer solution, a tris buffer solution, or a glycine buffer solution. The pH of a preservation solution may be 5 to 10, or 6 to 8.

The concentration of haptoglobin in the preservation solution depends on the type and amount of specimen, and examples thereof include 0.05 units/L to 50 units/L, 0.1 units/L to 10 units/L, or 0.2 units/L to 2 units/L. Here, one unit means an amount of haptoglobin binding to 1 mg of hemoglobin. The concentration of haptoglobin in the above-described ranges is a concentration sufficient for making all hemoglobin in a specimen form a complex with haptoglobin.

For example, in a case where feces are suspended in a preservation solution such that the concentration of feces becomes 0.05% to 25% (W/V %) with respect to 0.2 to 20 mL of the preservation solution, the proportion of the amount of haptoglobin in a specimen may be 0.075 g/unit to 5,000 g/unit.

Haptoglobin of the present invention is not particularly limited as long as it combines with hemoglobin to be assayed to generate a hemoglobin-haptoglobin complex. Since species specificity of the binding of hemoglobin to haptoglobin is low, a wide range of haptoglobin can be used. When human hemoglobin is a measurement target, haptoglobin derived from humans, horses, pigs, monkeys, dogs, rabbits, and rats can be used. It is unnecessary to use highly purified haptoglobin.

Well-known additives, for example, antibacterial agents such as sodium azide ($NaN_3$), pH adjusters, and salts for adjusting ionic strength, which can be used when preserving hemoglobin may be further added to a preservation solution. An antibacterial agent includes antibiotics and lytic enzymes. Examples of additives include well-known components, for example, amino acids such as lysine and histidine, albumin, a protease inhibitor, a water-soluble complex of transition metal ions, and ethylenediamine tetraacetic acid (EDTA), which are known to have a stabilizing effect on hemoglobin. Examples of albumin include serum albumin such as bovine serum albumin (BSA) and albumin (ovalbumin) derived from egg white.

<Hemoglobin Measurement Reagent>

The hemoglobin measurement reagent of one embodiment of the present invention includes: an insoluble carrier immobilizing an anti-hemoglobin antibody; and an insoluble carrier immobilizing an anti-haptoglobin antibody. An immunological method is used as a measurement method in which the reagent of the present invention is used. The immunological method may be a well-known immunological method using an anti-hemoglobin antibody, and examples thereof include an immunoagglutination method (for example, a latex agglutination method or a colloidal gold agglutination method), immunochromatography, and an ELISA method. In particularly, the reagent of the present invention is suitably used for an immunoagglutination method and more preferably for a latex agglutination method.

A hemoglobin measurement reagent of one embodiment of the present invention measures the total amount of hemoglobin using both free hemoglobin and a hemoglobin-haptoglobin complex as an measurement target during measurement The reagent of the present invention exhibits almost the same reactivity as hemoglobin to each antigen of free hemoglobin, a complete hemoglobin-haptoglobin complex, and a hemoglobin-haptoglobin complex intermediate in an immunological measurement method (particularly an immunoagglutination method). In particular, due to coexistence of the anti-haptoglobin antibody bound to an insoluble carrier, an excellent effect of showing the same reactivity ("equivalent reactivity to hemoglobin") to both antigens of a complete hemoglobin-haptoglobin complex and a hemoglobin-haptoglobin complex intermediate as hemoglobin is exhibited.

The "same reactivity as hemoglobin" means that, in a case where each antigen of free hemoglobin, a complete hemoglobin-haptoglobin complex, a hemoglobin-haptoglobin complex intermediate, or a mixture thereof is present in a sample as hemoglobin at equal concentrations, the concentrations of hemoglobin measured through an immunoagglutination reaction of insoluble carriers are substantially equal in each antigen. Here, when the concentrations of hemoglobin measured through an immunoagglutination reaction of insoluble carriers are "substantially equal", this means that, in a case where a measured value of free hemoglobin is 100%, a lower limit of a measured value of the concentration of hemoglobin when various other antigens having an identical concentration of hemoglobin are measured is greater than or equal to 80%, preferably greater than or equal to 90%, and more preferably greater than or equal to 95%, and an upper limit value of the measured value is less than or equal to 120%, preferably less than or equal to 110%, and more preferably less than or equal to 105%.

Due to incorporation of an insoluble carrier immobilizing an anti-haptoglobin antibody in addition to an insoluble carrier immobilizing an anti-hemoglobin antibody in the related art into the reagent of the present invention, the decrease in a measured value of hemoglobin caused by the addition of haptoglobin in the related art can be suppressed. In particular, even in a case where the molar ratio (hemoglobin/haptoglobin) of free hemoglobin in a specimen to haptoglobin to be added is less than 1, that is, in a case where a hemoglobin-haptoglobin complex intermediate is present, the decrease in a measured value of hemoglobin can be suppressed, and hemoglobin in the specimen can be accurately detected and measured.

Furthermore, in a case where haptoglobin is not added to a specimen, even if haptoglobin (regardless of free haptoglobin, a hemoglobin-haptoglobin complex intermediate, or a hemoglobin-haptoglobin complex) was originally present in the specimen, the decrease in a measured value of hemoglobin can be suppressed, and hemoglobin in the specimen can be accurately detected and measured.

The present inventors consider that the existence of a hemoglobin-haptoglobin complex intermediate is one of the causes of the decrease in a measured value of hemoglobin caused by the addition of haptoglobin in the related art and have solved this problem by adding an insoluble carrier immobilizing an anti-haptoglobin antibody.

An insoluble carrier that can immobilize an anti-hemoglobin antibody or an anti-haptoglobin antibody may be used. Insoluble particles that can be used for an immunological method are preferable, and examples thereof include colloidal metal particles such as colloidal gold particles, latex particles, silica particles, magnetic particles, fluorescent particles, and red blood cells, but the present invention is not limited thereto. As the insoluble particles, latex particles are preferable, and polystyrene latex particles are more preferable. The insoluble carriers are preferably in the form of particles. An average particle diameter thereof is preferably 5 to 1,000 nm, more preferably 30 to 500 nm, and still more preferably 75 to 350 nm, but the insoluble carriers can be used without being particularly limited to these ranges.

Immobilizing an antibody means that an antibody is bound (immobilized) through physical adsorption or chemical bonding to the surface of an insoluble carrier. As the immobilizing method (binding method), for example, antibodies can be mixed with insoluble carrier particles and can be physically adsorbed onto the surfaces of the insoluble carrier particles to bind the antibodies on the insoluble carrier particles, which is well-known technology. In addition, in a case of using insoluble carrier particles into which an amino group or a carboxyl group is introduced on the surfaces, antibodies can be bound on the surfaces of the insoluble carrier particles through chemical bonding in which a glutaraldehyde or carboxyimide reagent is used.

The amount of antibodies immobilized is not particularly limited, but may be 0.5 to 2,000 µg/mg latex, and may be 1 to 1,000 µg/mg latex or 2 to 500 µg/mg latex. The amount of antibodies immobilized can be calculated with an amount obtained by subtracting the amount of antibodies after binding from the amount of antibodies before binding on insoluble carriers.

Although not particularly limited, an anti-hemoglobin antibody can recognize an epitope of hemoglobin in a hemoglobin-haptoglobin complex, and preferably does not cross-react with haptoglobin. An anti-hemoglobin antibody may be a polyclonal antibody or a monoclonal antibody, but is preferably a monoclonal antibody or an anti-human hemoglobin monoclonal antibody from the viewpoint of specificity. The number of kinds of the anti-hemoglobin antibodies contained in a measurement reagent is at least one and preferably at least two.

On the other hand, although not particularly limited, an anti-haptoglobin antibody can recognize an epitope of haptoglobin in a hemoglobin-haptoglobin complex, and preferably does not cross-react with hemoglobin. In particular, an anti-haptoglobin antibody preferably does not agglutinate with free haptoglobin at an insoluble carrier on which the anti-haptoglobin antibody is immobilized, at least in the range of the amount of free haptoglobin used for forming a hemoglobin-haptoglobin complex. Furthermore, an anti-haptoglobin antibody preferably does not agglutinate at all with free haptoglobin at an insoluble carrier on which the anti-haptoglobin antibody is immobilized. An anti-haptoglobin antibody may be a polyclonal antibody or a monoclonal antibody, but is preferably a monoclonal antibody or an anti-haptoglobin monoclonal antibody. In the case where an anti-haptoglobin antibody is a monoclonal antibody, a recognition site thereof may be an $\alpha$ chain ($\alpha$ chain recognition antibody) or a $\beta$ chain ($\beta$ chain recognition antibody) of haptoglobin. The number of kinds of the anti-haptoglobin antibodies contained in a measurement reagent is at least one.

Animal species from which the above-described antibodies that can be used in the present invention are derived are not particularly limited, but examples thereof include antibodies derived from animals such as rabbits, goats, mice, rats, horses, and sheep. Both a polyclonal antibody obtained from the serum of an animal immunized with a measurement target and a monoclonal antibody obtained by cell fusion of the spleen of an animal immunized with a measurement target with myeloma cells through a well-known method may be used. In addition, fragments thereof [for example, F(ab')2, Fab, Fab', or Fv] can be used.

The number of kinds of insoluble carriers used for immobilizing anti-hemoglobin antibodies is at least one, but may be at least two. One or more kinds of anti-hemoglobin antibodies may be immobilized on one kind of insoluble carrier. In addition, one kind of anti-hemoglobin antibody may be immobilized on one or more kinds of insoluble carriers.

In the case where two or more kinds of anti-hemoglobin antibodies are contained in a measurement reagent, the two or more kinds of anti-hemoglobin antibodies may be immobilized on an identical insoluble carrier. Alternatively, plural kinds of insoluble carriers on which one kind of anti-hemoglobin antibody is immobilized on one kind of insoluble carrier can be combined and used. At this time, the insoluble carriers used for immobilizing different kinds of anti-hemoglobin antibodies may be the same kinds of insoluble carriers, or may be different kinds of insoluble carriers having different materials, particle diameters, or the like.

The number of kinds of insoluble carriers used for immobilizing anti-haptoglobin antibodies is at least one, but may be at least two. One or more kinds of anti-haptoglobin antibodies may be immobilized on one kind of insoluble carrier. In addition, one kind of anti-haptoglobin antibody may be immobilized on one or more kinds of insoluble carriers. In the case where two or more kinds of anti-haptoglobin antibodies are contained in a measurement reagent, the same applies to the above-described case where two or more kinds of anti-hemoglobin antibodies are contained in a measurement reagent.

The form of measurement reagent is not particularly limited, but may be, for example, a two-reagent system consisting of a reagent (first reagent) containing no insoluble carrier and a reagent (second reagent) containing an insoluble carrier (antibody-immobilizing insoluble carrier) immobilizing an antibody, or may be a one-reagent system consisting of only a reagent containing an antibody-immobilizing insoluble carrier.

The first reagent can be used so as to adjust a measurement environment, for example, can be used as a diluent from the viewpoints of, for example, adjusting the concentration of a measurement target or a contaminant or adjusting the reaction rate in a reaction system. The second reagent contains an antibody-immobilizing insoluble carrier, and is mixed with the first reagent and a sample to cause an immunoagglutination reaction. The first and second reagents can appropriately contain a pH buffer agent, a salt, a surfactant, an aggregation accelerator, a preservative, and the like. The pH thereof at the time of an agglutination reaction is preferably 5 to 9.

In addition, a measurement reagent is mixed with a preservation solution to obtain a reaction solution. The concentration of insoluble carriers in the reaction solution can be appropriately selected from a range of, for example, 0.0001 mg/mL to 10 mg/mL according to the particle diameters of insoluble carriers to be used or the design of the entire measurement system. The concentration of insoluble carriers immobilizing anti-hemoglobin antibodies in a measurement reagent may be 0.01 to 20 mg/mL or 0.05 to 1 mg/mL, and the concentration of insoluble carriers immobilizing anti-haptoglobin antibodies may be 0.01 to 20 mg/mL or 0.05 to 1 mg/mL.

The concentration of insoluble carriers in a second reagent is diluted by mixing with a preservation solution or mixing a first reagent with a preservation solution when in use. Therefore, the concentration of the insoluble carriers in the second reagent can be appropriately selected depending on the dilution magnification. For example, the concentration can be appropriately adjusted so as to be 0.004 mg/mL to 80 mg/mL in a case of 2-fold dilution and 0.06 mg/mL to 120 mg/mL in a case of 3-fold dilution.

<Hemoglobin Measurement Method>

[Step (1)]

In a step (1), a specimen is mixed with haptoglobin and a hemoglobin-haptoglobin complex is formed to obtain a sample containing the hemoglobin-haptoglobin complex.

The mixing of a specimen with haptoglobin is as described in the item of the above-described [Sample]. Here, the hemoglobin-haptoglobin complex contained in the sample can contain both a complete hemoglobin-haptoglobin complex and a hemoglobin-haptoglobin complex intermediate. The sample can also contain free hemoglobin derived from a specimen, a hemoglobin-haptoglobin complex derived from a specimen, and other components derived from a specimen, and can further contain free haptoglobin which does not form a complex with hemoglobin.

Haptoglobin to be mixed with a specimen may be contained in a specimen preservation solution, and in a case where haptoglobin is added to a specimen in a form that haptoglobin is contained in a specimen preservation solution, the sample can also contain other components of a preservation solution in addition to free haptoglobin which does not form a complex with hemoglobin. Since it is preferable that all free hemoglobin derived from a specimen form a complex with haptoglobin, the amount of haptoglobin to be mixed with a specimen may be an excess amount with respect to the free hemoglobin in a specimen.

[Step (2)]

In a step (2), the sample obtained in the step (1) is brought into contact with the insoluble carrier immobilizing an anti-hemoglobin antibody and the insoluble carrier immobilizing an anti-haptoglobin antibody to cause an immunoagglutination reaction.

The anti-hemoglobin antibody recognizes hemoglobin in the sample due to the above-described contact, whereby the insoluble carrier immobilizing an anti-hemoglobin antibody binds to hemoglobin or a hemoglobin-haptoglobin complex, and the insoluble carriers further agglutinate each other. The turbidity of a solution changes due to the agglutination of the insoluble carriers. Therefore, the change in turbidity of a solution can be assayed to obtain the concentration of hemoglobin in a sample using a calibration curve created using hemoglobin or a hemoglobin-haptoglobin complex with a known hemoglobin concentration.

Examples of measurement methods for the change in turbidity include a method for measuring an absorbance, scattered light, or the like of an immunoreaction solution through an optical technique. As the optical technique, for example, a general-purpose optical assay device may be used. For example, the assay can be performed using a biochemical automated clinical analyzer "JCA-BM2250" (manufactured by JEOL Ltd.) or "JCA-BM6070" (manufactured by JEOL Ltd.)

By bringing an insoluble carrier immobilizing an anti-haptoglobin antibody in addition to an insoluble carrier immobilizing an anti-hemoglobin antibody in the related art into contact with the sample in the measurement method of the present invention, the decrease in a measured value of hemoglobin caused by the addition of haptoglobin in the related art can be suppressed and hemoglobin in a specimen can be more accurately detected and measured. In a case where haptoglobin is not added to a specimen during measurement of hemoglobin in the specimen (that is, in a case where the step (1) is not performed), even if haptoglobin (regardless of free haptoglobin, a hemoglobin-haptoglobin complex intermediate, or a complete hemoglobin-haptoglobin complex) is originally present in the specimen, the specimen can be brought into contact with an insoluble carrier immobilizing an anti-hemoglobin antibody and an insoluble carrier immobilizing an anti-haptoglobin antibody and immunoagglutination can be caused (that is, only the step (2)) to suppress the decrease in a measured value of hemoglobin and accurately detect and measure hemoglobin in the specimen.

The present invention further provides a kit that can be used when detecting hemoglobin in a specimen by the above-described method. The kit may include a measurement reagent containing an anti-hemoglobin antibody-immobilizing insoluble carrier and an anti-haptoglobin antibody-immobilizing insoluble carrier, haptoglobin (preferably a preservation solution containing haptoglobin), a calibrator, a control, and the like, and may include a tool and a container for collecting a specimen, a preservation solution for preserving a specimen, and the like.

EXAMPLES

Examples 1-1 to 4-2 and Comparative Example 1

[Preparation of Measurement Reagents]

First and second reagents were prepared as measurement reagents.

A 50 mM HEPES buffer solution (pH of 7.4) was used as the first reagent.

The 50 mM HEPES buffer solution (pH of 7.4), polystyrene latex particles immobilizing respective antibodies of plural kinds of anti-hemoglobin monoclonal antibodies (anti-Hb antibodies), and polystyrene latex particles immobilizing anti-haptoglobin monoclonal antibodies were mixed at concentrations shown in Table 1 to prepare reagents for measuring immunoagglutination reaction of Examples 1-1 to 1-4 and Comparative Example 1 having final latex concentrations shown in Table 1, as the second reagent. Similarly, substances were mixed with each other at predetermined concentrations to prepare reagents for measuring immunoagglutination reaction of Examples 2-1 to 2-3, Examples 3-1 to 3-3, and Examples 4-1 to 4-2 having final latex concentrations shown in Table 2, as the second reagents.

AO-53 (α chain recognition), AO-27 (α chain recognition), AO-35 (α chain recognition), or AN12-8 (β chain recognition) was used as an anti-haptoglobin monoclonal antibody. Anti-haptoglobin antibodies in which it was confirmed that the amounts of free haptoglobin added as in the item of [Preparation of Samples] below did not agglutinate with insoluble carriers immobilizing the anti-haptoglobin antibodies were used.

Antibody-immobilizing polystyrene latex particles were prepared through a well-known method. That is, each anti-hemoglobin monoclonal antibody or anti-haptoglobin monoclonal antibody was mixed with polystyrene latex particles (average particle diameter of 200 nm) and immobilized on the surfaces of the polystyrene latex particles to prepare antibody-immobilizing polystyrene latex particles.

TABLE 1

| | Latex concentration (mg/mL) in second reagent | | | | |
| --- | --- | --- | --- | --- | --- |
| Antibody | Comparative Example 1 | Example 1-1 | Example 1-2 | Example 1-3 | Example 1-4 |
| Anti-Hb antibody | 0.69 | 0.69 | 0.69 | 0.69 | 0.69 |
| AO-53 | | 0.08 | 0.15 | 0.23 | 0.31 |

TABLE 2

| Antibody | Latex concentration (mg/mL) in second reagent | | | | | | | |
|---|---|---|---|---|---|---|---|---|
| | Example 2-1 | Example 2-2 | Example 2-3 | Example 3-1 | Example 3-2 | Example 3-3 | Example 4-1 | Example 4-2 |
| Anti-Hb antibody | 0.69 | 0.69 | 0.69 | 0.69 | 0.69 | 0.69 | 0.69 | 0.69 |
| AO-27 | 0.08 | 0.15 | 0.31 | | | | | |
| AO-35 | | | | 0.08 | 0.15 | 0.31 | | |
| AN12-8 | | | | | | | 0.08 | 0.15 |

[Preparation of Samples]

Human hemoglobin (hHb) purified from human blood and human haptoglobin (hHp) (Haptoglobin Human Phenotype 1-1 (manufactured by SIGMA Corporation)) were mixed with an Hb calibrator diluent 'Eiken' (manufactured by Eiken Chemical Co., Ltd.) so as to have concentrations shown in Table 3 to prepare samples Nos. 0 to 6. In No. 3, 0.8 units/L of human haptoglobin is mixed with 800 μg/L of human hemoglobin, and all of hemoglobin and haptoglobin form complete hemoglobin-haptoglobin complexes.

[Immunoagglutination]

Measurement reagents of Examples 1-1 to 1-4, Examples 2-1 to 2-3, Examples 3-1 to 3-3, Examples 4-1 and 4-2, and Comparative Example 1 were respectively added to the samples Nos. 0 to 6, and the turbidity was measured using an automated clinical analyzer BM2250 to calculate hemoglobin concentration conversion values based on the calibration curve which has been created in advance. Furthermore, relative values (%) of hemoglobin with respect to No. 0 (sample containing no human haptoglobin) were also calculated. The results are shown in Table 3.

The measurement conditions in JCA-BM2250 are as follows.

Amount of specimen: 2.0 μL
First reagent: 60 μL
Second reagent: 30 μL
Measurement wavelength: 658 nm

TABLE 3

| No. | hHb (μg/L) | hHp (units/L) | Results | Example 1-1 | Example 1-2 | Example 1-3 | Example 1-4 | Example 2-1 | Example 2-2 | Example 2-3 |
|---|---|---|---|---|---|---|---|---|---|---|
| 0 | 800 | 0 | hHb | 879 | 904 | 906 | 891 | 881 | 880 | 863 |
| 1 | 800 | 0.267 | concentration | 870 | 890 | 888 | 899 | 865 | 867 | 841 |
| 2 | 800 | 0.533 | conversion | 874 | 875 | 890 | 879 | 837 | 856 | 838 |
| 3 | 800 | 0.8 | value | 842 | 867 | 877 | 864 | 818 | 831 | 830 |
| 4 | 800 | 1.067 | (μg/L) | 843 | 874 | 868 | 862 | 822 | 819 | 827 |
| 5 | 800 | 1.333 | | 830 | 850 | 873 | 851 | 812 | 829 | 836 |
| 6 | 800 | 1.6 | | 814 | 845 | 857 | 825 | 795 | 815 | 833 |
| 0 | 800 | 0 | Relative | 100% | 100% | 100% | 100% | 100% | 100% | 100% |
| 1 | 800 | 0.267 | value | 99% | 98% | 98% | 101% | 98% | 98% | 97% |
| 2 | 800 | 0.533 | of | 99% | 97% | 98% | 99% | 95% | 97% | 97% |
| 3 | 800 | 0.8 | hHb | 96% | 96% | 97% | 97% | 93% | 94% | 96% |
| 4 | 800 | 1.067 | with | 96% | 97% | 96% | 97% | 93% | 93% | 96% |
| 5 | 800 | 1.333 | respect | 94% | 94% | 96% | 95% | 92% | 94% | 97% |
| 6 | 800 | 1.6 | to No. 0 | 93% | 93% | 95% | 93% | 90% | 93% | 96% |

| No. | hHb (μg/L) | hHp (units/L) | Results | Example 3-1 | Example 3-2 | Example 3-3 | Example 4-1 | Example 4-2 | Comparative Example 1 |
|---|---|---|---|---|---|---|---|---|---|
| 0 | 800 | 0 | hHb | 899 | 900 | 869 | 878 | 891 | 893 |
| 1 | 800 | 0.267 | concentration | 875 | 860 | 854 | 866 | 881 | 853 |
| 2 | 800 | 0.533 | conversion | 850 | 841 | 823 | 871 | 873 | 826 |
| 3 | 800 | 0.8 | value | 820 | 816 | 804 | 848 | 882 | 794 |
| 4 | 800 | 1.067 | (μg/L) | 801 | 799 | 795 | 844 | 885 | 787 |
| 5 | 800 | 1.333 | | 798 | 807 | 801 | 847 | 898 | 795 |
| 6 | 800 | 1.6 | | 760 | 784 | 798 | 855 | 903 | 724 |
| 0 | 800 | 0 | Relative | 100% | 100% | 100% | 100% | 100% | 100% |
| 1 | 800 | 0.267 | value | 97% | 96% | 98% | 99% | 99% | 96% |
| 2 | 800 | 0.533 | of | 95% | 94% | 95% | 99% | 98% | 92% |
| 3 | 800 | 0.8 | hHb | 91% | 91% | 92% | 97% | 99% | 89% |
| 4 | 800 | 1.067 | with | 89% | 89% | 91% | 96% | 99% | 88% |
| 5 | 800 | 1.333 | respect | 89% | 90% | 92% | 96% | 101% | 89% |
| 6 | 800 | 1.6 | to No. 0 | 84% | 87% | 92% | 97% | 101% | 81% |

It became clear from Table 3 that, each of the examples, in which latex immobilizing an anti-haptoglobin antibody was added together with latex immobilizing an anti-hemoglobin antibody and which was a case where haptoglobin was added when measuring hemoglobin, can suppress decrease in a hemoglobin assay value due to the addition of haptoglobin, that is, can obtain a measured value closer to the actual value compared to Comparative Example 1 in which only latex immobilizing an anti-hemoglobin antibody is added but no latex immobilizing an anti-haptoglobin antibody is added. These results were obtained using either the anti-haptoglobin antibody which was a chain recognition or β chain recognition, demonstrating that the results did not depend on the subunits recognized by the anti-haptoglobin antibodies.

Comparative Examples 2-1 to 2-3, 3-1 to 3-3, and 4 to 7

Reagents obtained by mixing free anti-haptoglobin antibodies which were not immobilized on latex instead of the anti-haptoglobin antibody-immobilizing latex of Example 1-1 with anti-hemoglobin antibody-immobilizing latex were prepared and added to the samples Nos. 0 to 6 to similarly cause agglutination reactions, and hemoglobin concentration conversion values and relative values (%) of hemoglobin were calculated. The compositions of the reagents of each of the comparative examples are shown in Table 4, and the results are shown in Table 5. Anti-haptoglobin antibodies AN11-2 and AN12-3 were β chain recognition anti-haptoglobin monoclonal antibodies and prepared through a well-known method.

From Table 5, even if free anti-haptoglobin antibodies which have not been bound to latex were added, it was impossible to suppress the decrease in a measured value of hemoglobin due to the addition of haptoglobin. Rather, it showed a tendency that the values became lower. It is assumed that this is probably because bonding between anti-hemoglobin antibodies bound to latex and hemoglobin-haptoglobin complexes was inhibited by the excess anti-haptoglobin antibodies.

TABLE 4

|  | Antibody | Comparative Example 2-1 | Comparative Example 2-2 | Comparative Example 2-3 | Comparative Example 3-1 | Comparative Example 3-2 |
|---|---|---|---|---|---|---|
| Latex concentration (mg/mL) | Anti-Hb antibody | 0.69 | 0.69 | 0.69 | 0.69 | 0.69 |
| Concentration (μg/mL) of anti-haptoglobin antibody | AO-53 | 5 | 10 | 20 | | |
| | AN11-2 | | | | 5 | 10 |
| | AN12-3 | | | | | |
| | AO-27 | | | | | |
| | AO-35 | | | | | |
| | AN12-8 | | | | | |

|  | Antibody | Comparative Example 3-3 | Comparative Example 4 | Comparative Example 5 | Comparative Example 6 | Comparative Example 7 |
|---|---|---|---|---|---|---|
| Latex concentration (mg/mL) | Anti-Hb antibody | 0.69 | 0.69 | 0.69 | 0.69 | 0.69 |
| Concentration (μg/mL) of anti-haptoglobin antibody | AO-53 | | | | | |
| | AN11-2 | 20 | | | | |
| | AN12-3 | | 20 | | | |
| | AO-27 | | | 20 | | |
| | AO-35 | | | | 20 | |
| | AN12-8 | | | | | 20 |

TABLE 5

| No. | hHb (μg/L) | hHp (units/L) | Results | Comparative Example 1 | Comparative Example 2-1 | Comparative Example 2-2 | Comparative Example 2-3 | Comparative Example 3-1 | Comparative Example 3-2 |
|---|---|---|---|---|---|---|---|---|---|
| 0 | 800 | 0 | hHb | 893 | 884 | 884 | 906 | 892 | 894 |
| 1 | 800 | 0.267 | concentration | 853 | 826 | 804 | 809 | 838 | 824 |
| 2 | 800 | 0.533 | conversion | 826 | 756 | 739 | 755 | 788 | 758 |
| 3 | 800 | 0.8 | value | 794 | 695 | 682 | 660 | 713 | 662 |
| 4 | 800 | 1.067 | (μg/L) | 787 | 663 | 642 | 623 | 688 | 622 |
| 5 | 800 | 1.333 | | 795 | 640 | 608 | 598 | 675 | 582 |
| 6 | 800 | 1.6 | | 724 | 506 | 471 | 437 | 543 | 412 |
| 0 | 800 | 0 | Relative | 100% | 100% | 100% | 100% | 100% | 100% |
| 1 | 800 | 0.267 | value | 96% | 93% | 91% | 89% | 94% | 92% |
| 2 | 800 | 0.533 | of | 92% | 85% | 84% | 83% | 88% | 85% |
| 3 | 800 | 0.8 | hHb | 89% | 79% | 77% | 73% | 80% | 74% |
| 4 | 800 | 1.067 | with | 88% | 75% | 73% | 69% | 77% | 70% |
| 5 | 800 | 1.333 | respect | 89% | 72% | 69% | 66% | 76% | 65% |
| 6 | 800 | 1.6 | to No. 0 | 81% | 57% | 53% | 48% | 61% | 46% |

| No. | hHb (μg/L) | hHp (units/L) | Results | Comparative Example 3-3 | Comparative Example 4 | Comparative Example 5 | Comparative Example 6 | Comparative Example 7 |
|---|---|---|---|---|---|---|---|---|
| 0 | 800 | 0 | hHb | 911 | 896 | 887 | 880 | 879 |
| 1 | 800 | 0.267 | concentration | 811 | 818 | 837 | 818 | 832 |
| 2 | 800 | 0.533 | conversion | 703 | 741 | 824 | 768 | 751 |
| 3 | 800 | 0.8 | value | 589 | 652 | 807 | 715 | 698 |
| 4 | 800 | 1.067 | (μg/L) | 533 | 608 | 799 | 693 | 670 |
| 5 | 800 | 1.333 | | 482 | 579 | 804 | 669 | 648 |
| 6 | 800 | 1.6 | | 323 | 405 | 766 | 569 | 523 |
| 0 | 800 | 0 | Relative | 100% | 100% | 100% | 100% | 100% |
| 1 | 800 | 0.267 | value | 89% | 91% | 94% | 93% | 95% |
| 2 | 800 | 0.533 | of | 77% | 83% | 93% | 87% | 85% |
| 3 | 800 | 0.8 | hHb | 65% | 73% | 91% | 81% | 79% |
| 4 | 800 | 1.067 | with | 58% | 68% | 90% | 79% | 76% |

TABLE 5-continued

| 5 | 800 | 1.333 | respect | 53% | 65% | 91% | 76% | 74% |
| 6 | 800 | 1.6 | to No. 0 | 35% | 45% | 86% | 65% | 60% |

Examples 5-1 to 5-5 and Comparative Example 8

[Preparation of Measurement Reagents]

A first and second reagents were prepared as measurement reagents.

A 50 mM HEPES buffer solution (pH of 7.4) was used as the first reagent.

The 50 mM HEPES buffer solution (pH of 7.4), polystyrene latex particles immobilizing respective antibodies of plural kinds of anti-hemoglobin monoclonal antibodies (anti-Hb antibodies), and polystyrene latex particles immobilizing anti-haptoglobin monoclonal antibodies were mixed at concentrations shown in Table 6 to prepare reagents for measuring immunoagglutination reaction of Examples 5-1 to 5-5 and Comparative Example 8 having final latex concentrations shown in Table 6, as the second reagent.

AO-53 (α chain recognition) or AN12-8 (β chain recognition) was used as an anti-haptoglobin monoclonal antibody. Anti-haptoglobin antibodies in which it was confirmed that the amounts of free haptoglobin added as in the item of [Preparation of Samples] below did not agglutinate with insoluble carriers immobilizing the anti-haptoglobin antibodies were used.

The confirmation method was performed in the same manner as in preparation of samples and an immunoagglutination method to be described below except that 1.0 mg/mL of polystyrene latex on which AO-53 (α chain recognition) or AN12-8 (β chain recognition) were immobilized was used as a second reagent and that samples (containing no hemoglobin) obtained by adding free haptoglobin to a preservation solution (Hb calibrator diluent 'Eiken' (manufactured by Eiken Chemical Co., Ltd.)) so as to have a concentration of 0 ng/mL or 24.5 pmol/mL were used. The haptoglobin concentration of 24.5 pmol/mL corresponds to a free haptoglobin addition concentration of 1.2 units/L.

Antibody-immobilizing polystyrene latex particles were prepared by a well-known method. That is, each anti-hemoglobin monoclonal antibody or anti-haptoglobin monoclonal antibody was mixed with polystyrene latex particles (average particle diameter of 200 nm) and immobilized on the surfaces of the polystyrene latex particles to prepare antibody-immobilizing polystyrene latex particles.

[Preparation of Samples]

Two fecal specimens (fecal specimens 1 and 2) were collected from a healthy person. Each of the fecal specimens, human hemoglobin (hHb) purified from human blood, and human haptoglobin (hHp) (Haptoglobin Human Phenotype 1-1 (manufactured by SIGMA Corporation)) were mixed with a preservation solution (Hb calibrator diluent 'Eiken' (manufactured by Eiken Chemical Co., Ltd.)) so as to respectively have a fecal concentration of 0.5% (W/V %) and concentrations shown in Tables 7 and 8 to prepare samples Nos. 0 to 5. In No. 3, 0.6 units/L of human haptoglobin is mixed with 600 µg/L of human hemoglobin, and all of hemoglobin and haptoglobin form complete hemoglobin-haptoglobin complexes.

[Immunoagglutination]

Measurement reagents of Examples 5-1 to 5-5 and Comparative Example 8 were respectively added to the samples Nos. 0 to 5 of the fecal specimens 1 and 2, and the turbidity was measured using an automated clinical analyzer JCA-BM6070 to calculate hemoglobin concentration conversion values based on the calibration curve which has been created in advance. Furthermore, relative values (%) of hemoglobin with respect to No. 0 (sample containing no human haptoglobin) were also calculated. The results are shown in Tables 7 and 8.

The measurement conditions in JCA-BM6070 are as follows.

Amount of specimen: 2.0 µL

First reagent: 60 µL

Second reagent: 30 µL

Measurement wavelength: 658 nm

TABLE 6

| | Latex concentration (mg/mL) in second reagent | | | | | |
|---|---|---|---|---|---|---|
| Antibody | Comparative Example 8 | Example 5-1 | Example 5-2 | Example 5-3 | Example 5-4 | Example 5-5 |
| Anti-Hb antibody | 0.69 | 0.69 | 0.69 | 0.69 | 0.69 | 0.69 |
| AO-53 | | 0.08 | 0.15 | 0.23 | 0.31 | |
| AN12-8 | | | | | | 0.08 |

TABLE 7

Fecal specimen 1

| No. | hHb (µg/L) | hHp (units/L) | Results | Comparative Example 8 | Example 5-1 | Example 5-2 | Example 5-3 | Example 5-4 | Example 5-5 |
|---|---|---|---|---|---|---|---|---|---|
| 0 | 600 | 0.0 | hHb | 568 | 560 | 563 | 566 | 563 | 570 |
| 1 | 600 | 0.2 | concentration | 546 | 552 | 559 | 561 | 557 | 565 |
| 2 | 600 | 0.4 | conversion | 524 | 548 | 555 | 556 | 551 | 567 |
| 3 | 600 | 0.6 | value | 437 | 545 | 564 | 570 | 560 | 562 |
| 4 | 600 | 0.7 | (µg/L) | 414 | 541 | 557 | 563 | 560 | 557 |
| 5 | 600 | 0.8 | | 401 | 538 | 556 | 565 | 558 | 555 |
| 0 | 600 | 0.0 | Relative | 100% | 100% | 100% | 100% | 100% | 100% |
| 1 | 600 | 0.2 | value | 96% | 99% | 99% | 99% | 99% | 99% |
| 2 | 600 | 0.4 | of hHb | 92% | 98% | 99% | 98% | 98% | 100% |
| 3 | 600 | 0.6 | with | 77% | 97% | 100% | 101% | 99% | 99% |
| 4 | 600 | 0.7 | respect | 73% | 96% | 99% | 99% | 99% | 98% |
| 5 | 600 | 0.8 | to No. 0 | 71% | 96% | 99% | 100% | 99% | 97% |

TABLE 8

Fecal specimen 2

| No. | hHb (µg/L) | hHp (units/L) | Results | Comparative Example 8 | Example 5-1 | Example 5-2 | Example 5-3 | Example 5-4 | Example 5-5 |
|---|---|---|---|---|---|---|---|---|---|
| 0 | 600 | 0.0 | hHb | 567 | 560 | 564 | 562 | 568 | 571 |
| 1 | 600 | 0.2 | concentration | 550 | 556 | 562 | 566 | 564 | 572 |
| 2 | 600 | 0.4 | conversion | 528 | 551 | 559 | 557 | 554 | 572 |
| 3 | 600 | 0.6 | value | 430 | 540 | 559 | 559 | 556 | 560 |
| 4 | 600 | 0.7 | (µg/L) | 405 | 536 | 554 | 555 | 554 | 556 |
| 5 | 600 | 0.8 | | 380 | 515 | 545 | 550 | 547 | 546 |
| 0 | 600 | 0.0 | Relative | 100% | 100% | 100% | 100% | 100% | 100% |
| 1 | 600 | 0.2 | value of | 97% | 99% | 100% | 101% | 99% | 100% |
| 2 | 600 | 0.4 | hHb | 93% | 98% | 99% | 99% | 97% | 100% |
| 3 | 600 | 0.6 | with | 76% | 96% | 99% | 99% | 98% | 98% |
| 4 | 600 | 0.7 | respect | 71% | 96% | 98% | 99% | 98% | 97% |
| 5 | 600 | 0.8 | to No. 0 | 67% | 92% | 97% | 98% | 96% | 96% |

The invention claimed is:

1. A reagent for measuring a total amount of hemoglobin, wherein the total amount of hemoglobin is the total amount of a hemoglobin-haptoglobin complex and free hemoglobin, comprising:
a mixture of a first insoluble carrier immobilizing an anti-hemoglobin antibody and a second insoluble carrier immobilizing an anti-haptoglobin antibody.

2. The reagent according to claim 1, wherein the insoluble carriers are latex particles and/or colloidal gold particles.

3. The reagent according to claim 1, wherein the anti-hemoglobin antibody and the anti-haptoglobin antibody are monoclonal antibodies.

4. The reagent according to claim 1, wherein the number of kinds of the anti-haptoglobin antibodies is one.

5. A hemoglobin measurement method for measuring a total amount of hemoglobin in a specimen, wherein the total amount of hemoglobin is the total amount of a hemoglobin-haptoglobin complex and free hemoglobin, the method comprising:
a step (1) of mixing a specimen with haptoglobin and forming a hemoglobin-haptoglobin complex to obtain a sample containing the hemoglobin-haptoglobin complex;
a step (2) of mixing the sample obtained in the step (1) with a first insoluble carrier immobilizing an anti-hemoglobin antibody and a second insoluble carrier immobilizing an anti-haptoglobin antibody; and
a step (3) of measuring the total amount of hemoglobin-haptoglobin complex and the free hemoglobin.

6. The measurement method according to claim 5, wherein the insoluble carriers are latex particles and/or colloidal gold particles.

7. The measurement method according to claim 5, wherein the anti-hemoglobin antibody and the anti-haptoglobin antibody are monoclonal antibodies.

8. The measurement method according to claim 5, wherein the specimen is feces, saliva, or urine.

9. The measurement method according to claim 5, wherein haptoglobin is contained in a specimen preservation solution.

10. The measurement method according to claim 9, wherein a concentration of haptoglobin in the specimen preservation solution is 0.05 units/L to 50 units/L.

11. The measurement method according to claim 5, wherein hemoglobin in the specimen contains at least one selected from the group consisting of free hemoglobin, a hemoglobin-haptoglobin complex intermediate, and a complete hemoglobin-haptoglobin complex, and
wherein at least a part of the free hemoglobin forms the hemoglobin-haptoglobin complex intermediate and/or the complete hemoglobin-haptoglobin complex together with the haptoglobin after the step (1).

12. A method for suppressing a decrease in a measured value of the total amount of a hemoglobin-haptoglobin complex and free hemoglobin in a specimen, the method comprising:
mixing a specimen with a first insoluble carrier carrying an anti-hemoglobin antibody and a second insoluble carrier carrying an anti-haptoglobin antibody to cause immunoagglutination; and measuring a total amount of the hemoglobin-haptoglobin complex and the free hemoglobin.

13. The reagent according to claim 1, wherein the anti-hemoglobin antibody recognizes an epitope of hemoglobin in a hemoglobin-haptoglobin complex and does not cross-react with haptoglobin, and wherein the anti-haptoglobin antibody recognizes an epitope of haptoglobin in a hemoglobin-haptoglobin complex and does not agglutinate with free haptoglobin.

14. The measurement method according to claim 5, wherein the anti-hemoglobin antibody recognizes an epitope of hemoglobin in a hemoglobin-haptoglobin complex and does not cross-react with haptoglobin, and wherein the anti-haptoglobin antibody recognizes an epitope of haptoglobin in a hemoglobin-haptoglobin complex and does not agglutinate with free haptoglobin.

15. The method according to claim 12, wherein the anti-hemoglobin antibody recognizes an epitope of hemoglobin in a hemoglobin-haptoglobin complex and does not cross-react with haptoglobin, and wherein the anti-haptoglobin antibody recognizes an epitope of haptoglobin in a hemoglobin-haptoglobin complex and does not agglutinate with free haptoglobin.

\* \* \* \* \*